United States Patent
Iwasaki

(10) Patent No.: US 9,505,038 B2
(45) Date of Patent: Nov. 29, 2016

(54) ENDOSCOPE CLEANING TUBE

(71) Applicant: OLYMPUS CORPORATION, Tokyo (JP)

(72) Inventor: Tomokazu Iwasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/141,047

(22) Filed: Apr. 28, 2016

(65) Prior Publication Data

US 2016/0236248 A1    Aug. 18, 2016

Related U.S. Application Data

(63) Continuation of application No. PCT/JP2015/061078, filed on Apr. 9, 2015.

(30) Foreign Application Priority Data

Jul. 16, 2014   (JP) ................. 2014-146201

(51) Int. Cl.
  *B08B 9/032* (2006.01)
  *B08B 9/023* (2006.01)
  *A61B 1/12* (2006.01)

(52) U.S. Cl.
  CPC ............ *B08B 9/0323* (2013.01); *A61B 1/123* (2013.01); *A61B 1/125* (2013.01); *B08B 9/023* (2013.01)

(58) Field of Classification Search
  CPC ...... A61B 1/121; A61B 1/122; A61B 1/123; A61B 1/125; B08B 9/012; B08B 9/027; B08B 9/032; B08B 9/0321; B08B 9/0323
  See application file for complete search history.

(56) References Cited

U.S. PATENT DOCUMENTS

2009/0205687 A1   8/2009   Onishi et al.

FOREIGN PATENT DOCUMENTS

| EP | 2 098 185 A1 | 9/2009 |
|---|---|---|
| JP | 58-116335 A | 7/1983 |
| JP | 58-155836 A | 9/1983 |
| JP | 58-180129 A | 10/1983 |
| JP | 2004-135946 A | 5/2004 |
| JP | 2009-195400 A | 9/2009 |

OTHER PUBLICATIONS

International Search Report dated Jun. 30, 2015 issued in PCT/JP2015/061078.
Japanese Office Action dated Oct. 27, 2015 issued in JP 2015-537859.

*Primary Examiner* — David Cormier
(74) *Attorney, Agent, or Firm* — Scully, Scott, Murphy & Presser, P.C.

(57) ABSTRACT

An endoscope cleaning tube according to the invention includes a housing portion; a movable portion adapted to divide an inner part of the housing portion into a side of the fluid introduction port and a side of the fluid lead-out port and placed between a first position and a second position in the housing portion, the second position being located closer to the side of the fluid lead-out port than the first position; a pressure-receiving portion which, being equipped with a pressure-receiving surface placed at a position facing the fluid introduction port and adapted to receive pressure of the fluid, is adapted to pivot according to fluid pressure on the pressure-receiving surface; and a linking portion adapted to connect the movable portion and the pressure-receiving portion with each other and move the movable portion from the second position to the first position when the pressure-receiving portion receives the fluid pressure.

3 Claims, 16 Drawing Sheets

ENDOSCOPE CLEANING TUBE

CROSS REFERENCE TO RELATED APPLICATION

This application is a continuation application of PCT/JP2015/061078 filed on Apr. 9, 2015 and claims benefit of Japanese Application No. 2014-146201 filed in Japan on Jul. 16, 2014, the entire contents of which are incorporated herein by this reference.

BACKGROUND OF THE INVENTION

1. Field of the Invention

The present invention relates to an endoscope cleaning tube adapted to deliver a fluid such as a cleaning liquid or disinfecting solution into a conduit of an endoscope by connecting to a pipe sleeve communicated with the conduit in the endoscope.

2. Description of the Related Art

After each use, an endoscope needs to undergo reprocessing such as a cleaning process, disinfecting process, sterilization process, or a combination of these processes.

Such a reprocessing process is often performed using an apparatus adapted to automatically perform reprocessing. The endoscope is set in a cleaning tank in a reprocessing apparatus in a predetermined manner, communicates a pipe sleeve communicated with each conduit such as an air/water feeding conduit, a suction conduit, or a treatment instrument insertion conduit provided in the endoscope with a corresponding fluid supply port provided in the reprocessing apparatus via a cleaning tube, and thereby supplied a fluid to each conduit provided in the endoscope and performs reprocessing.

Also, a technique is known which, in fitting a housing portion provided at one end of the cleaning tube into the pipe sleeve communicated with each conduit and supplying the fluid into the conduit, provides a gap between the cleaning tube and pipe sleeve, allows the fluid to leak through the gap, and thereby cleans a surface of the pipe sleeve simultaneously. For example, Japanese Patent Application Laid-Open Publication No. 2009-195400 discloses a technique which includes a housing portion (casing body) placed at one end of a cleaning tube and configured to be connectable to a pipe sleeve; and a movable portion (valve disk) placed in the housing portion and configured to move toward the pipe sleeve under pumping pressure, wherein when a liquid such as a cleaning liquid or a disinfecting solution is supplied into the housing portion from a side of a reprocessing apparatus, the movable portion moves in a direction of the pipe sleeve under liquid pressure, forms a predetermined gap in an opposing surface between the pipe sleeve and the movable portion by being kept in balance with a compression spring and thereby being kept from coming into close contact with a surface of the pipe sleeve, allows a fluid to leak through the gap, and thereby allows the surface of the pipe sleeve to be cleaned or disinfected as well.

Now, in cleaning and disinfecting the various conduits provided in the endoscope, if foreign matter remains in any of the conduits, narrowing inner part of the conduit, it becomes impossible to supply a sufficient amount of fluid into the conduit, and cleaning and disinfection of the endoscope will be hindered. Therefore, according to Patent Application Laid-Open Publication No. 2009-195400 described above, a flow sensor adapted to measure a flow rate of the fluid supplied to each conduit is provided in the reprocessing apparatus to monitor flow condition of the fluid and thereby detect any clogging of the conduit.

There is demand for an endoscope cleaning tube which usually allows circumference of a pipe sleeve to be cleaned and disinfected by forming a gap between the pipe sleeve and movable portion, and keeps the movable portion pressed against the pipe sleeve in case of clogging of the conduit, allowing the clogging of the conduit to be detected accurately.

SUMMARY OF THE INVENTION

An endoscope cleaning tube according to one aspect of the invention includes a housing portion equipped with a fluid introduction port adapted to introduce a fluid and a fluid lead-out port adapted to lead out the fluid introduced through the fluid introduction port; a hook portion extending out from an outer surface of the housing portion in a lead-out direction of the fluid to connect the housing portion to a pipe sleeve; a movable portion placed movably between a first position and a second position in the housing portion, being equipped with a partition portion adapted to divide an inner part of the housing portion into a side of the fluid introduction port and a side of the fluid lead-out port and with an opening portion which is an opening provided in the partition portion, the second position being located closer to the side of the fluid lead-out port than the first position; a pressure-receiving portion which, being equipped with a pressure-receiving surface placed at a position facing the fluid introduction port and adapted to receive pressure of the introduced fluid and with a first end portion pivotably connected to an inner wall of the housing portion, is adapted to pivot according to an amount of the fluid pressure acting on the pressure-receiving surface; and a linking portion adapted to connect the pressure-receiving portion and the movable portion with each other and move the movable portion from the second position to the first position along with pivoting of the pressure-receiving portion when the pressure-receiving portion receives fluid pressure equal to or larger than a predetermined amount.

DETAILED DESCRIPTION OF THE PREFERRED EMBODIMENTS

An embodiment of the present invention will be described below with reference to the drawings. In the following description, note that the drawings in each embodiment are schematic, that a relationship between thickness and width of each component as well as ratios of the thickness among individual components are different from actual ones, and that dimensional relationships or ratios may not be uniform among the drawings.

First Embodiment

Figure 1:
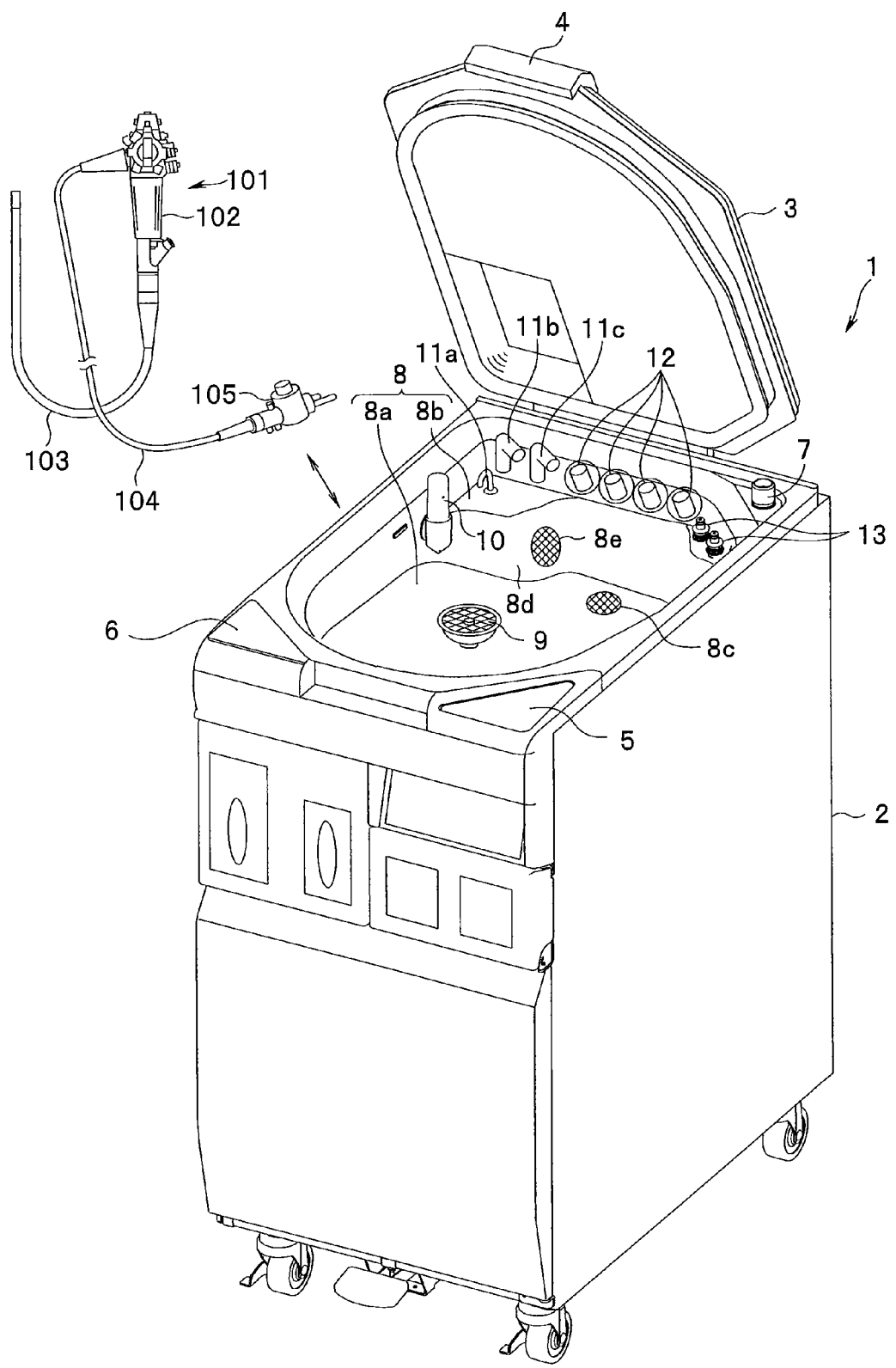
FIG. 1 is a perspective view of a reprocessing apparatus and endoscope according to a first embodiment.

A first embodiment of the present invention is shown in FIG. 1 to FIG. 9. As shown in FIG. 1, an endoscope reprocessing apparatus 1 is intended to perform a reprocess to allow an endoscope 101 after use to be inserted into a subject again. The reprocess as referred to herein can be selected appropriately depending on a contaminated state of the endoscope and a site into which the endoscope 101 is inserted. For example, at least one of cleaning, disinfection, and sterilization can be selected, where the cleaning is used to remove contaminants such as protein, disinfection is used to neutralize harmful bacteria and viruses, and sterilization is used to kill bacteria and viruses.

Principal part of the endoscope reprocessing apparatus 1 is made up of an apparatus body 2, a processing tank 8 provided in the apparatus body 2, and a top cover 3 adapted to open and close the processing tank 8.

With rear part of the top cover 3 pivotably supported, front part of the top cover 3 is configured to be able to open and close. When the top cover 3 is closed, a latch portion 4 provided in the front part is locked to the apparatus body 2 to maintain watertight condition. Note that the apparatus body 2 contains various tanks used to store various liquids such as a cleaning liquid and disinfecting solution; various pumps used to supply various liquids from various tanks to the processing tank 8 and conduits in endoscope 101; a control section adapted to control various pumps and various valves according to each step in cleaning/disinfecting steps; and the like.

In upper front part of the apparatus body 2, a main operation portion 5 which is usually operated is provided on the observers' right and a wireless ID transmitting/receiving portion 6 serving as an information reading portion is provided on the observers' left. Various switches and a display area are disposed in a predetermined manner on the main operation portion 5, where the various switches include a start switch and a stop switch used, respectively, to start and stop a reprocess such as cleaning, disinfection, or sterilization of the apparatus body 2 as well as a selector switch used to select a reprocess mode of cleaning, disinfection, sterilization, or the like.

The wireless ID transmitting/receiving portion 6 reads identification information (user ID) about a worker when an ID card owned by the worker is brought close to the wireless ID transmitting/receiving portion 6, and reads endoscope identification information (scope ID) from a scope ID tag contained in an endoscope brought close to the wireless ID transmitting/receiving portion 6. Note that if no scope ID tag is contained in the endoscope, after causing the user ID to be read, the worker can manually input the scope ID of the endoscope from outside using a switch provided on the main operation portion 5 and make the control section recognize the scope ID.

Figure 2:
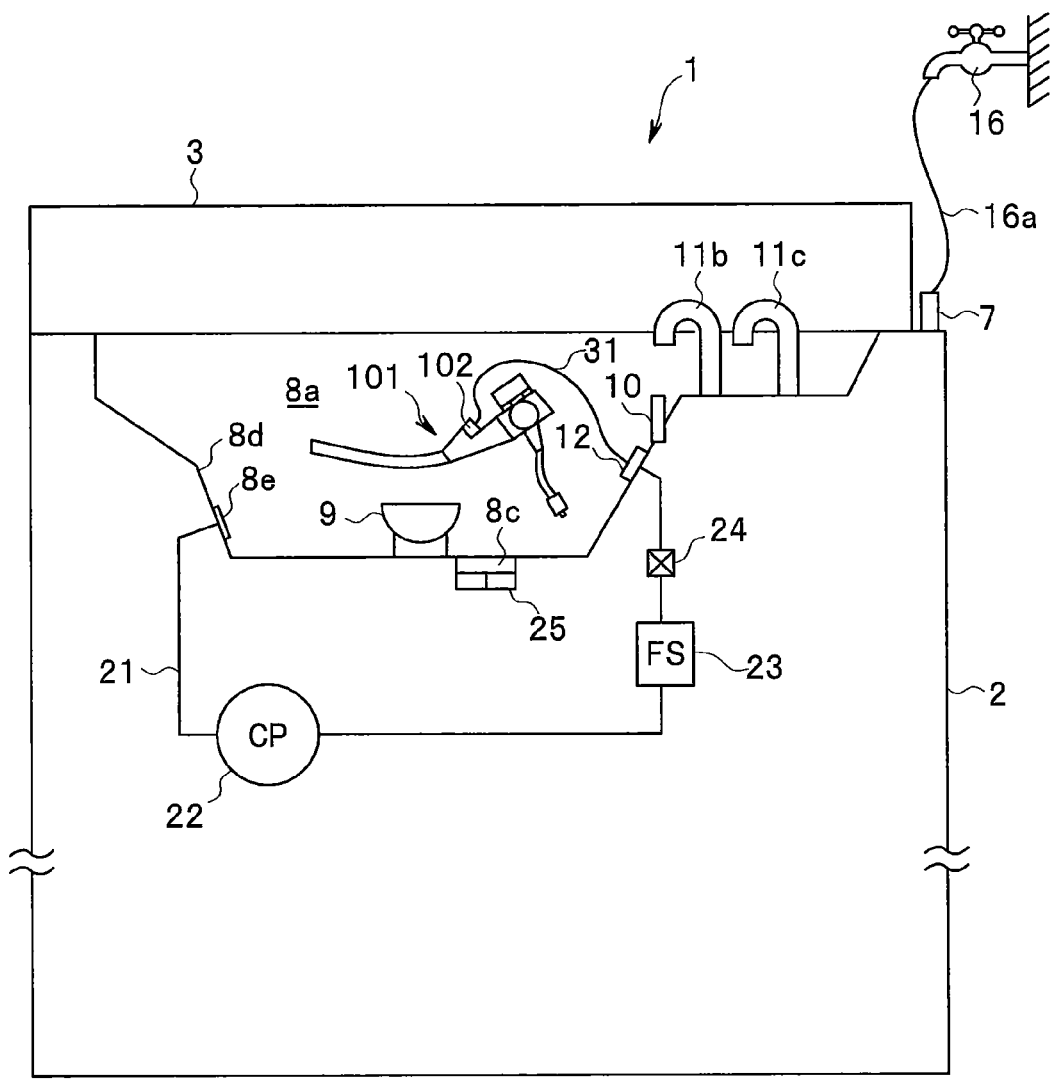
FIG. 2 is a schematic diagram of principal part showing an internal configuration of the reprocessing apparatus according to the first embodiment.

At a rear right end of the apparatus body 2, a water supply hose connection port 7 is disposed to supply tap water to the apparatus body 2. Note that the water supply hose connection port 7 is connected to a water supply hose 16a connected to a water faucet 16 as shown in FIG. 2. Furthermore, the processing tank 8 is provided at an approximate center of the apparatus body 2. The processing tank 8 illustrated in FIG. 1 by example is capable of reprocessing plural endoscopes 101 at a time and includes a tank body 8a capable of accommodating plural endoscopes 101 and a terrace portion 8b provided behind the tank body 8a.

Although not illustrated, an endoscope holding net is installed on the tank body 8a, and the endoscope 101 is set on the endoscope holding net in a predetermined manner after use. A typical endoscope 101 is shown in FIG. 1. An operation portion 102 for use by an operator to grip and operate is provided on the user's hand side of the endoscope 101 and an insertion portion 103 to be inserted into the body is extended out from the operation portion 102. Also, a universal cord 104 is extended from lateral part of the operation portion 102, and a connector portion 105 is fixedly installed at a terminating end of the universal cord 104. Note that in addition to the typical endoscope 101 described above, endoscopes to be reprocessed include endoscopes not equipped with a universal cord 104.

The tank body 8a described above is formed in a depressed shape and a drain hole 8c is provided in a bottom portion of the depression, allowing liquids such as the cleaning liquid, water, alcohol, or disinfecting solution supplied to the tank body 8a to be discharged through the drain hole 8c. Furthermore, a circulation port 8e is provided in a wall surface 8d of the tank body 8a. The circulation port 8e allows the liquid such as the water, cleaning liquid, or disinfecting solution supplied to the tank body 8a to recirculate through each conduit installed inside the endoscope 101, using means described later or allow the liquid supplied to the tank body 8a to be supplied again from a feed water circulation nozzle 11c described later to the tank body 8a through a mesh filter and the like.

Furthermore, a non-illustrated case conduit is provided in an approximate center portion of a bottom face of the tank body 8a and an accessory cleaning case (hereinafter referred to as a "cleaning case") 9 is fitted in the case conduit. Accessories of the endoscope 101 are placed in the cleaning case 9. A liquid such as a disinfecting solution is supplied into the cleaning case 9 through the case conduit from a pump provided in the apparatus body 2, and the placed accessories are reprocessed together with the endoscope 101.

A water level sensor 10 adapted to measure a water level of the liquid supplied to the tank body 8a is provided on a side face of the tank body 8a. Furthermore, a detergent nozzle 11a and disinfecting solution nozzle 11b are disposed in the terrace portion 8b, where the detergent nozzle 11a supplies a cleaning agent by a detergent pump from a detergent tank stored in the apparatus body 2 to the processing tank 8 while the disinfecting solution nozzle 11b supplies a disinfecting solution by a medical solution pump from a medical solution tank housed in the apparatus body 2 to the processing tank 8. Furthermore, the feed water circulation nozzle 11c is disposed in the terrace portion 8b to supply water to the processing tank 8 or supply liquid sucked through the circulation port 8e of the tank body 8a to the processing tank 8 again.

Plural ports 12 (four according to the present embodiment) and a water leak detection port 13 are disposed in the terrace portion 8b, where the plural ports 12 supply fluids such as water, a cleaning liquid, alcohol, disinfecting solution, or air to plural conduits installed inside the endoscope 101. The plural ports 12 are connector portions adapted to supply a cleaning liquid and the like to respective conduits including a suction conduit, a secondary water feeding conduit, an air/water feeding conduit, and a forceps port, and are respectively connected, via a cleaning tube 31, to known pipe sleeves communicated with the suction conduit, air/water feeding conduit, forceps port, and secondary water feeding conduit provided in the endoscope 101. Note that FIG. 2 shows in a simplified manner how a pipe sleeve provided in the forceps port in the operation portion 102 is connected with a port 12 via the cleaning tube 31.

As shown in FIG. 2, the circulation port 8e is communicated with each port 12 through a circulation conduit 21 disposed in the apparatus body 2, and a conduit pump 22, a flow sensor 23, and a conduit solenoid valve 24 are interposed in the circulation conduit 21 starting from the side of the circulation port 8e, i.e., from an upstream side. The conduit pump 22 sucks a liquid stored in the processing tank 8, and delivers the liquid to the side of the circulation port 8e. The flow sensor 23 is designed to measure a flow rate of the fluid flowing through the circulation conduit 21 per unit time, and measurement results are transmitted to a non-illustrated control unit.

The control unit checks the conduit for clogging based on the received flow rate measured by the flow sensor 23 and displays an error message in the display area of the main operation portion 5, indicating the clogging of the conduit. A method for checking a conduit for clogging is not particularly limited, and a conventionally known method may be used. For example, clogging may be checked for by a method which compares the flow rate with a threshold.

The drain hole 8c is configured to be able to be communicated selectively with the medical solution tank and an external drain conduit via a selector valve 25: when communicated with the medical solution tank, the drain hole 8c allows the fluid in the processing tank 8 to be recovered, and when communicated with the external drain conduit, the drain hole 8c allows the fluid to be discharged outside. Also, the fluid recovered to the medical solution tank is supplied to the processing tank 8 again through the disinfecting solution nozzle 11b.

Figure 3:
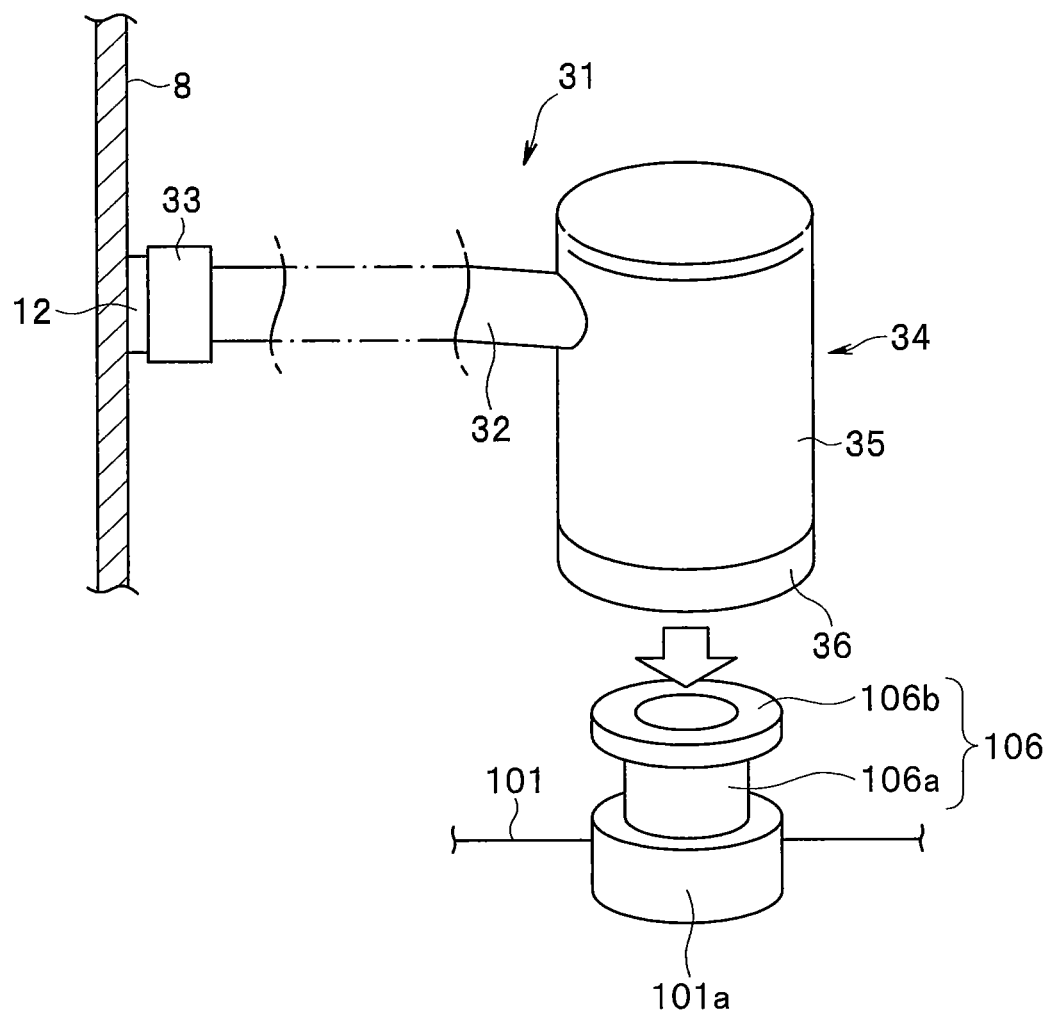
FIG. 3 is a perspective view of how an endoscope-side junction of a cleaning tube is connected to a pipe sleeve of the endoscope according to the first embodiment.

As shown in FIG. 3, the cleaning tube 31 includes a tube main body 32 having flexibility. An apparatus-side connector portion 33 connectable to the ports 12 provided in the endoscope reprocessing apparatus 1 is fixedly installed at one end of the tube main body 32 and an endoscope-side connector portion 34 connectable with a pipe sleeve 106 provided in an open end portion of each conduit such as the suction conduit, air/water feeding conduit, forceps port, or secondary water feeding conduit of the endoscope 101 is fixedly installed at the other end. The pipe sleeve 106 includes a barrel portion 106a adapted to connect to an opening portion 101a of each conduit by being fixedly installed in the endoscope 101 and a flange portion 106b is formed at an upper end of the barrel portion 106a. Note that a structure of the apparatus-side connector portion 33 connectable to the ports 12 is the same as a conventional one, and thus description thereof will be omitted herein.

Figure 4:
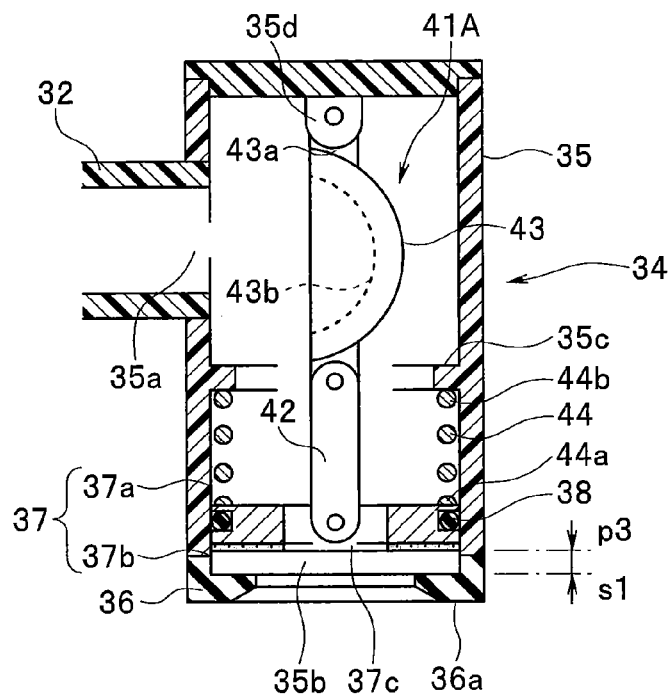
FIG. 4 is a sectional side view showing the endoscope-side junction of the cleaning tube according to the first embodiment.
Figure 5:
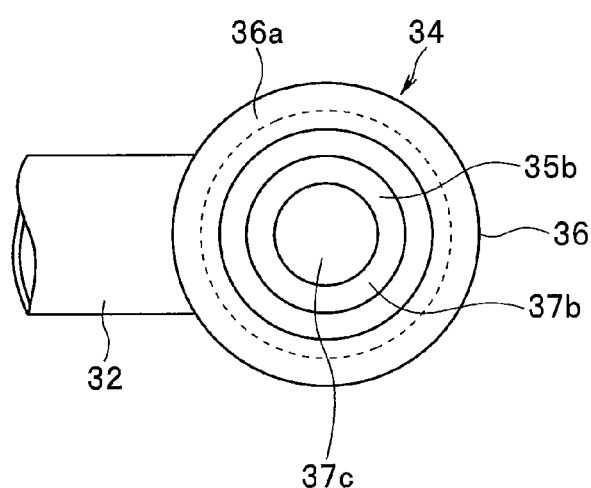
FIG. 5 is a bottom view of FIG. 4 according to the first embodiment.

As shown in FIG. 4, the endoscope-side connector portion 34 includes a housing portion 35. Material of the housing portion is not particularly limited, and resin or metal may be used, for example. As shown in FIG. 5, the housing portion 35 is formed into a substantially cylindrical shape whose lower end is open, a fluid introduction port 35a is formed in upper part of a side face, and a lower end of an opening makes up a fluid lead-out port 35b. The fluid lead-out port 35b is fixedly installed at the other end of the tube main body 32, the fluid sent from a side of the tube main body 32 is introduced into the housing portion 35 through the fluid introduction port 35a, and the fluid introduced into inner part is lead out through the fluid lead-out port 35b. Examples of the fluid include water, cleaning liquid, disinfecting solution, alcohol, and any of these liquids mixed with gas.

Furthermore, a hook portion 36 extends out downward from an outer surface of a lower end of the fluid lead-out port 35b. Preferably, the hook portion 36 is an elastic body. Examples of materials for the hook portion 36 includes polymers having elasticity. The hook portion 36 is formed in the shape of a tray whose bottom center is open. A locking portion 36a is formed in a bottom portion of the hook portion 36 and the locking portion 36a latches onto an undersurface of the flange portion 106b formed on an open end of the pipe sleeve 106. Also, a bottom face of the locking portion 36a is tapered to guide the flange portion 106b when the flange portion 106b is fitted in the housing portion 35 from outside. Alternatively, the hook portion 36 may be formed in the shape of a claw. In this case, any material having flexibility can be used, and resin or metal is suitable.

A spring catching portion 35c is formed between the fluid introduction port 35a and fluid lead-out port 35b in an inner wall of the housing portion 35, protruding inward in the form of a ring. Furthermore, a movable portion 37 is interposed between the spring catching portion 35c and fluid lead-out port 35b. The movable portion 37 is configured to be able to perform rectilinear motion in an up-and-down direction by being guided by the inner wall of the housing portion 35, and is equipped with a partition portion 37a formed into a disk shape and adapted to separate a side of the fluid introduction port 35a and a side of the fluid lead-out port 35b as well as with a sealing portion 37b bonded to a bottom face of the partition portion 37a.

An opening portion 37c is opened in centers of the partition portion 37a and sealing portion 37b. On the other hand, spacing between an outer circumference of the partition portion 37a and the inner wall of the housing portion 35 is sealed by a seal ring 38 fitted on the outer circumference of partition portion 37a.

Figure 6:
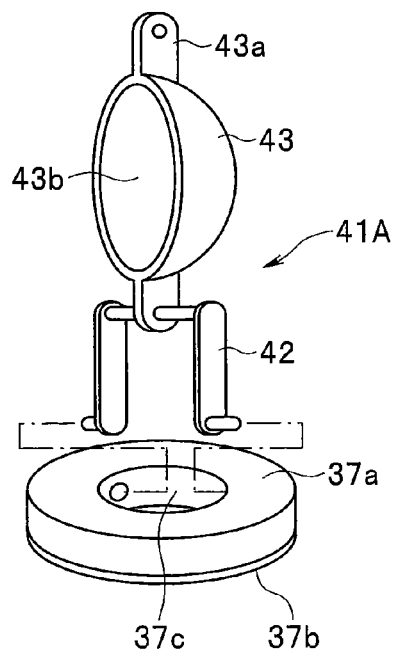
FIG. 6 is a perspective view of a movable portion, a pressure-receiving portion, and a link connecting the two portions in the endoscope-side junction of the cleaning tube according to the first embodiment.

A center of the movable portion 37 is connected to a suspension bracket 35d protruding from a ceiling of the housing portion 35, via a linkage mechanism 41A. As shown in FIG. 6, the linkage mechanism 41A includes a link portion 42 whose lower part is pivotally supported by an inner wall of the opening portion 37c of the movable portion 37 and a pressure-receiving portion 43 whose lower end portion is connected to an upper end portion of the link portion 42, and an upper bracket 43a as a first end portion of the pressure-receiving portion 43 is pivotably supported by the suspension bracket 35d. The pressure-receiving portion 43 is placed face to face with the fluid introduction port 35a in such a way as to be able to move in and out of contact with the fluid introduction port 35a, and a pressure-receiving surface 43b is formed at a position facing the fluid introduction port 35a.

Figure 8:
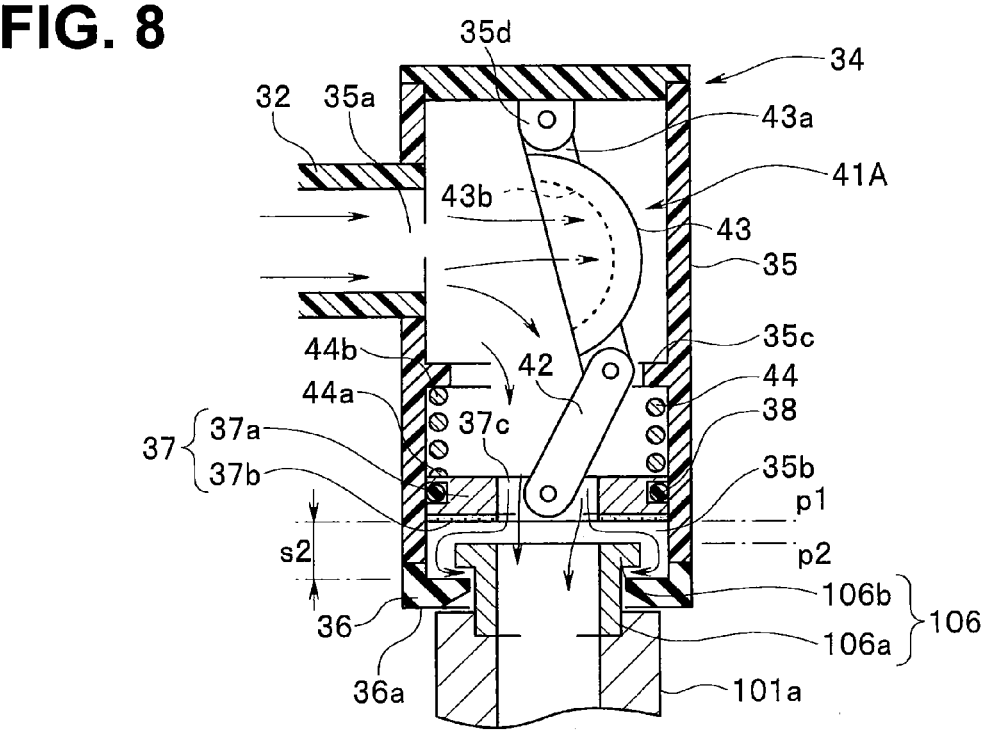
FIG. 8 is a sectional side view of how the endoscope-side junction of the cleaning tube is connected to the pipe sleeve of the endoscope according to the first embodiment.

The pressure-receiving surface 43b is formed into a cup shape to receive pressure of the fluid introduced into the housing portion 35 through the fluid introduction port 35a. As shown in FIG. 8, when the pressure-receiving surface 43b pivots to a side opposite the fluid introduction port 35a under the pressure of the fluid, the movable portion 37 connected via the link portion 42 slides upward by being guided by the inner wall of the housing portion 35.

Also, a compression spring 44, which is an example of a spring portion, is interposed between the movable portion 37 and spring catching portion 35c. Being configured such that a lower end portion 44a, which is a second end portion, will be connected to (abutted against) a top face of the movable portion 37 and that an upper end portion 44b, which is a third end portion, will be connected to (abutted against) the spring catching portion 35c, the compression spring 44 is positioned on the inner wall of the housing portion 35 so as to be positioned closer to the side of the fluid introduction port 35a than to the lower end portion 44a. The movable portion 37 is urged toward the fluid lead-out port 35b by the compression spring 44.

When fluid pressure received by the pressure-receiving surface 43b exceeds spring pressure of the compression spring 44 and loads caused by frictional resistance of respective sliding parts of the movable portion 37 and linkage mechanism 41A, the pressure-receiving portion 43 pivots in a pressing direction of the fluid pressure. On the other hand, when the spring pressure of the compression spring 44 exceeds the fluid pressure acting on the pressure-receiving surface 43b and the loads caused by the frictional resistance of the respective sliding parts of the movable portion 37 and linkage mechanism 41A, the pressure-receiving portion 43 is pushed back toward the fluid introduction port 35a.

Even if, for example, the housing portion 35 is fitted sideways into the pipe sleeve 106, when the pressure-receiving surface 43b is not under fluid pressure, the spring pressure of the compression spring 44 is set at a low value just about enough to make the movable portion 37 abut an upper end face of the pipe sleeve 106. Thus, when the pressure-receiving surface 43b is subjected to the pressure of the fluid, the movable portion 37 slides upward against an urging force of the compression spring 44.

Figure 9:
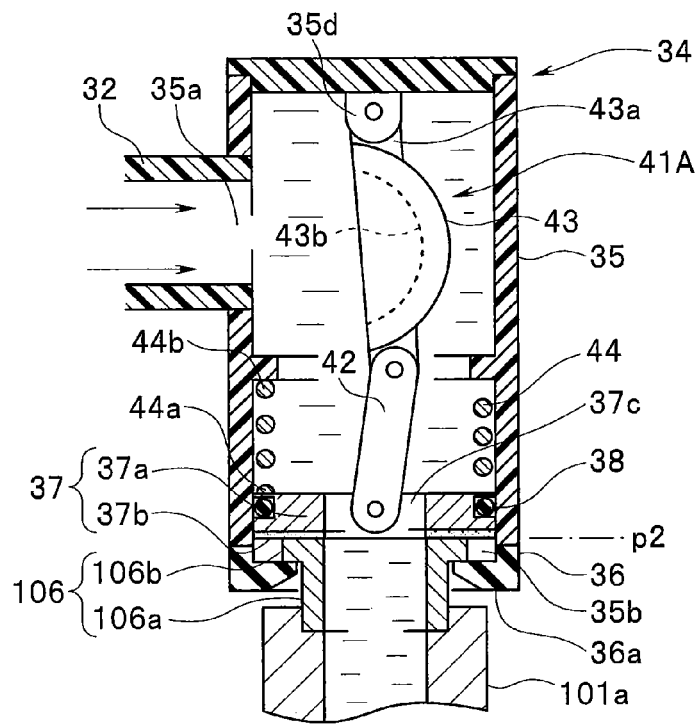
FIG. 9 is a sectional side view of FIG. 8 when clogging of a conduit occurs, according to the first embodiment.

Also, as shown in FIG. 4, when the housing portion 35 is not fitted in the pipe sleeve 106, because the linkage mechanism 41A is extended out rectilinearly toward the fluid lead-out port 35b, a bottom face of the movable portion 37 at this time is located at a third position p3, which is closest to the hook portion 36. In this state, a gap s1 between the third position p3 and a top face of the locking portion 36a provided on the hook portion 36 is set smaller than a height h1 (see FIG. 7) of the flange portion 106b formed on the pipe sleeve 106 (s1<h1). Thus, as shown in FIG. 9, with the housing portion 35 fitted in the flange portion 106b of the pipe sleeve 106, the bottom face of the movable portion 37 is placed at a second position p2 raised by a difference value (h1−s1) between the above-mentioned gap s1 and the height h1 of the pipe sleeve 106, causing a connecting site between the link portion 42 and pressure-receiving portion 43 of the linkage mechanism 41A to be bent slightly.

On the other hand, as shown in FIG. 8, when the pressure-receiving portion 43 is pivoted by the pressure of the fluid acting on the pressure-receiving surface 43b of the pressure-receiving portion 43 as the fluid is introduced into the housing portion 35 through the fluid introduction port 35a, the bottom face of the movable portion 37 moves up to a first position p1 by being spaced away from a top face of the pipe sleeve 106, creating a gap between the bottom face of the movable portion 37 and top face of the pipe sleeve 106. As a result, because a gap s2 between the top face of the locking portion 36a of the hook portion 36 and the bottom face of the movable portion 37 is larger than the height h1 of the flange portion 106b of the pipe sleeve 106, the flange portion 106b enters a so-called floating state, and part of the fluid flowing out from the opening portion 37c of the movable portion 37 toward a side of the fluid lead-out port 35b is discharged from between the locking portion 36a of the hook portion 36 and the barrel portion 106a of the pipe sleeve 106 by bypassing the pipe sleeve 106.

Next, operation of the present embodiment with such a configuration will be described. In reprocessing the endoscope 101 using the endoscope reprocessing apparatus 1 after use in an endoscopic examination, first the endoscope 101 is set in the processing tank 8 of the endoscope reprocessing apparatus 1 in a predetermined manner, and then the apparatus-side connector portion 33 provided at one end of the cleaning tube 31 is connected to each port 12 in the apparatus body 2. Next, the endoscope-side connector portion 34 provided at the other end of the cleaning tube 31 is connected to the pipe sleeve 106 provided in the opening portion 101a of each conduit in the endoscope 101 (see FIG. 3).

Figure 7:
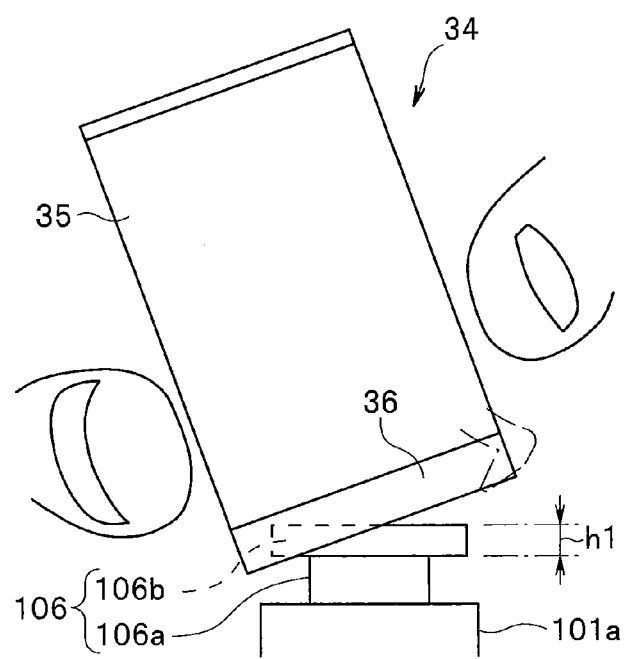
FIG. 7 is a front view of FIG. 4 according to the first embodiment.

As shown in FIG. 7, when fitting the endoscope-side connector portion 34 in the pipe sleeve 106, the worker grips the housing portion 35 with fingers, tilts the housing portion 35 to one side, latches the flange portion 106b formed on the pipe sleeve 106 onto the locking portion 36a formed on the hook portion 36, and then fits the locking portion 36a of the hook portion 36 in the flange portion 106b by elastically deforming the hook portion 36.

Also, as shown in FIG. 4, the link portion 42 and pressure-receiving portion 43 of the linkage mechanism 41A provided in the housing portion 35 of the endoscope-side connector portion 34 is extended out rectilinearly under the urging force of the compression spring 44, the gap s1 between the third position p3, which corresponds to a position of the bottom face of the movable portion 37 at this time, and the top face of the locking portion 36a formed on the hook portion 36 is set smaller than the height h1 of the flange portion 106b formed on the pipe sleeve 106 (s1<h1). Thus, when the flange portion 106b of the pipe sleeve 106 is fitted over the hook portion 36 of the endoscope-side connector portion 34, the sealing portion 37b provided on the bottom face of the movable portion 37 abuts the open end of the pipe sleeve 106, and then the open end of the pipe sleeve 106 pushes up the linkage mechanism 41A by an amount equivalent to the difference value (h1−s1) between the gap s1 and the height h1 of the flange portion 106b against the urging force of the compression spring 44. As a result, the linkage mechanism 41A is bent slightly by centering on a coupling portion between the link portion 42 and pressure-receiving portion 43 and the flange portion 106b is pinched between an inner surface of the locking portion 36a and the sealing portion 37b of the movable portion 37 (see FIG. 9).

Next, based on a program set by the worker, reprocessing is performed to clean, disinfect, or sterilize the endoscope 101. Note that reprocessing steps are similar to conventional ones, and thus description thereof will be omitted herein.

Once reprocessing is started, a conduit pump 22 interposed in a circulation conduit 21 provided in the apparatus body 2 of the endoscope reprocessing apparatus 1 as shown in FIG. 2 is driven. The circulation conduit 21 is communicated on an upstream side with the circulation port 8e provided in the wall surface 8d of the processing tank 8, and communicated on a downstream side with each port 12 provided in the terrace portion 8b of the processing tank 8. Thus, when the conduit solenoid valve 24 interposed in the circulation conduit 21 opens, the fluid (water, cleaning liquid, disinfecting solution, or the like) stored in the processing tank 8 is sucked in through the circulation port 8e and discharged from the port 12 through the circulation conduit 21.

Since the port 12 is connected with the one end of the cleaning tube 31 via the apparatus-side connector portion 33 and the endoscope-side connector portion 34 provided at the other end is fitted in each pipe sleeve 106 provided in the corresponding opening portion 101a communicated with the corresponding conduit in the endoscope 101, the fluid discharged through the port 12 is led from the apparatus-side connector portion 33 to the endoscope-side connector portion 34 through the tube main body 32 and introduced into the housing portion 35 through the fluid introduction port 35a formed in the housing portion 35 of the endoscope-side connector portion 34.

Then, as shown in FIG. 8, the pressure (dynamic pressure) of the fluid is applied to the pressure-receiving surface 43b formed in the pressure-receiving portion 43 of the linkage mechanism 41A placed in the housing portion 35, causing the pressure-receiving portion 43 to pivot in a counterclockwise direction in FIG. 8. Then, via the link portion 42 connected to the pressure-receiving portion 43 the movable portion 37 moves up against the urging force of the compression spring 44 by being circumferentially guided by the inner wall of the housing portion 35 and moves up from the second position p2 where the movable portion 37 is abutted against the open end of the pipe sleeve 106 to the first position p1, making the gap s2 between the top face of the locking portion 36a of the hook portion 36 and the bottom face of the movable portion 37 larger than the height h1 of the flange portion 106b of the pipe sleeve 106.

As a result, the flange portion 106b of the pipe sleeve 106 enters a so-called floating state in the gap s2, and part of the fluid introduced into the housing portion 35 and led out from the opening portion 37c, which opens in the movable portion 37, toward a side of the fluid lead-out port 35b is led to the conduit in the endoscope 101 through the pipe sleeve 106 and opening portion 101a, and is discharged to the tank body 8a after cleaning or disinfecting an interior of the conduit in a predetermined manner. On the other hand, the rest of the fluid led out to the fluid lead-out port 35b passes through a gap formed between the movable portion 37 and the open end of the pipe sleeve 106 as well as through a surface of the pipe sleeve 106, and is discharged outside through a gap between the locking portion 36a of the hook portion 36 and the barrel portion 106a of the pipe sleeve 106. Consequently, not only the interior of the conduit of the endoscope 101, but also circumference of the pipe sleeve 106 are cleaned or disinfected at the same time.

A flow rate of the fluid supplied to a side of the endoscope 101 through the cleaning tube 31 is measured by the flow sensor 23 interposed in the circulation conduit 21, and when the flow rate is equal to or lower than a threshold set beforehand, it is judged that the conduit in the endoscope 101 is clogged and an error message is displayed in the display area of the main operation portion 5.

That is, when clogging occurs in the conduit of the endoscope 101, the flow rate of the fluid supplied into the housing portion 35 is limited. As a result, the pressure (dynamic pressure) of the fluid acting on the pressure-receiving portion 43 provided in the linkage mechanism 41A decreases and a pressing force tending to cause the pressure-receiving portion 43 to pivot in the counterclockwise direction in FIG. 8 decreases. On the other hand, the fluid introduced into the housing portion 35 from the cleaning tube 31 fills the housing portion 35, gradually increasing internal pressure (static pressure). Because the internal pressure is applied uniformly to the inside of the housing portion 35 the movable portion 37 is pushed down under the internal pressure and the urging force of the compression spring 44.

Then, as shown in FIG. 9, the sealing portion 37b provided on the bottom face of the movable portion 37 abuts the open end of the pipe sleeve 106, limiting the fluid leaking to the surface of the pipe sleeve 106 through the opening portion 37c of the movable portion 37. As a result, because the fluid stagnates in the housing portion 35 and the flow rate of the fluid measured by the flow sensor 23 decreases extremely, it is judged that the conduit is clogged when the flow rate becomes, for example, equal to or lower than a threshold. Note that since the movable portion 37 is abutted against the pipe sleeve 106 by the differential pressure between the pressure on the side of the pipe sleeve 106 and the internal pressure in the housing portion 35 as well as the compression spring 44, when the pressure in the housing portion 35 increases, abutting pressure on the pipe sleeve 106 increases accordingly, more reliably blocking the fluid from leaking from around the pipe sleeve 106.

Thus, according to the present embodiment, since the linkage mechanism 41A is provided in the endoscope-side connector portion 34 of the cleaning tube 31 and the pressure-receiving portion 43 of the linkage mechanism 41A is designed to normally pivot under fluid pressure, forming a gap between the movable portion 37 and the open end of the pipe sleeve 106, the circumference of the pipe sleeve 106 is allowed to be cleaned or disinfected. On the other hand, if a conduit in the endoscope 101 clogs, the movable portion 37 is kept in pressing contact with the pipe sleeve 106 by internal pressure filling the housing portion 35, limiting leakage of the fluid from around the pipe sleeve 106. As a result, the flow rate of the fluid confined by the flow sensor 23 decreases extremely, and clogging of the conduit can be detected accurately based on the flow rate measured by the flow sensor 23.

Also, since the movable portion 37 is constantly urged toward a side of the fluid lead-out port 35b by the compression spring 44, when the conduit in the endoscope 101 clogs, the movable portion 37 can be quickly brought into pressing contact with the open end of the pipe sleeve 106 by the urging force of the compression spring 44, making it possible to provide good responsiveness. However, the present embodiment can bring the open end of the pipe sleeve 106 into pressing contact with the movable portion 37 without the urging force of the compression spring 11, and thus the compression spring 44 may be omitted.

Furthermore, by providing the sealing portion 37b on the bottom face of movable portion 37, it is possible to bring the movable portion 37 into close contact with the open end of the pipe sleeve 106 and reliably block leakage from around the pipe sleeve 106. However, the flow rate measured by the flow sensor 23 is decreased extremely even if the movable portion 37 is not brought into close contact with the open end of the pipe sleeve 106, and thus the movable portion 37 may be equipped with only the partition portion 37a by omitting the sealing portion 37b.

Second Embodiment

Figure 10:
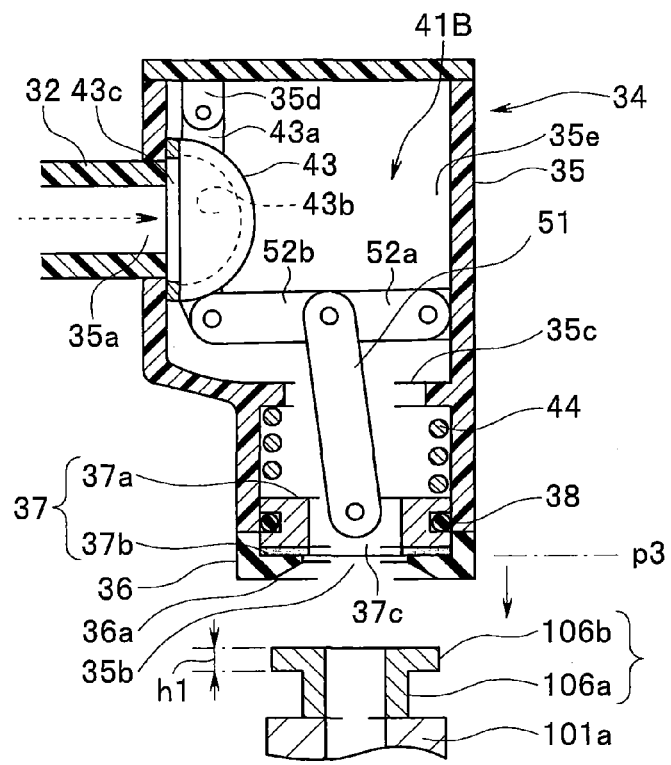
FIG. 10 is a sectional side view showing an endoscope-side junction of a cleaning tube according to a second embodiment.
Figure 11:
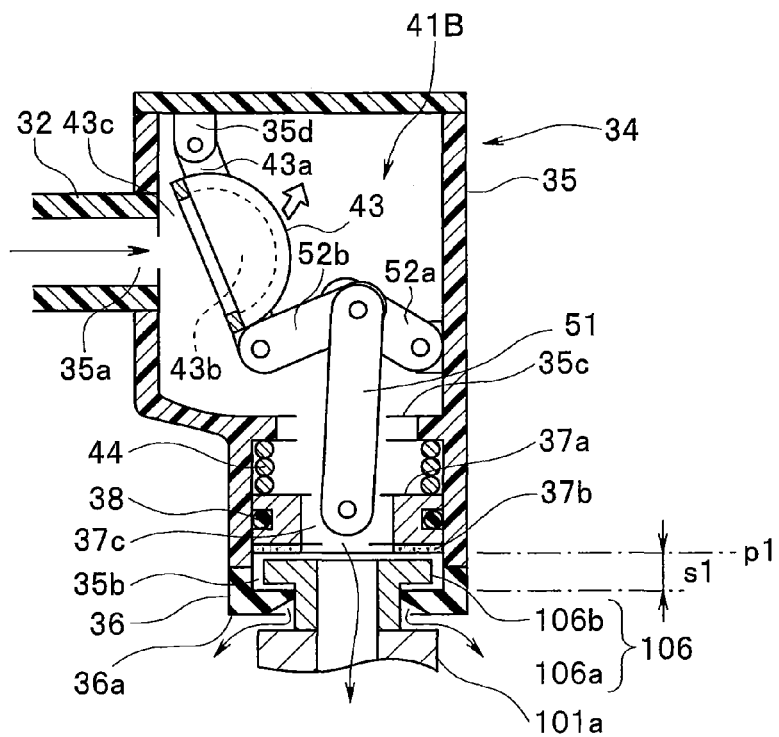
FIG. 11 is a sectional side view of how the endoscope-side junction of the cleaning tube is connected to a pipe sleeve according to the second embodiment.
Figure 12:
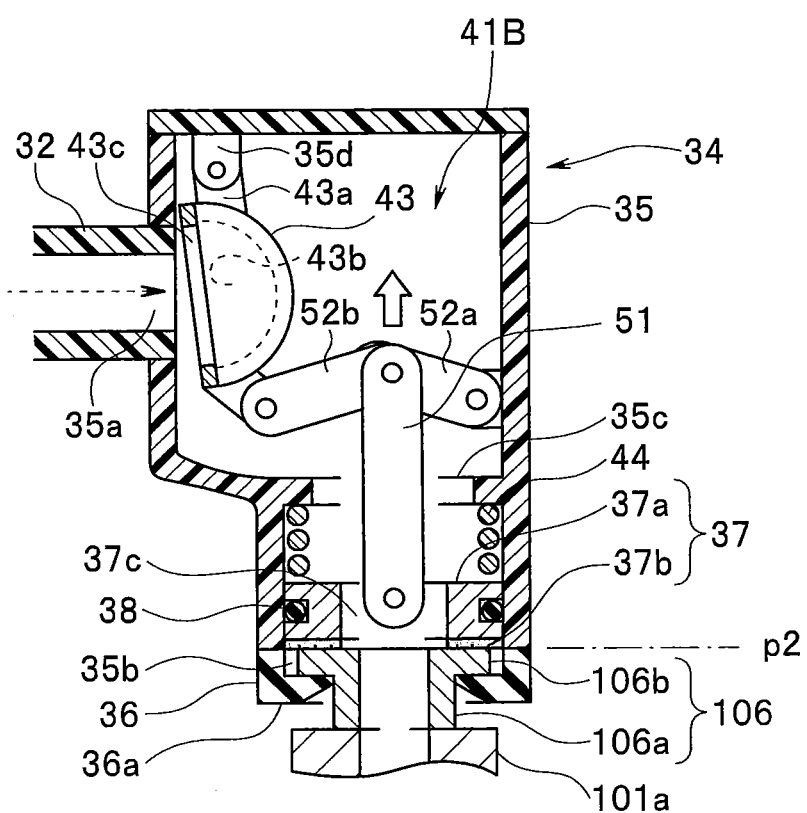
FIG. 12 is a sectional side view of FIG. 11 when clogging of a conduit occurs, according to the second embodiment.

A second embodiment of the present invention is shown in FIG. 10 to FIG. 12. With the cleaning tube 31 according to the first embodiment described above, for example, if the endoscope-side connector portion 34 comes off the pipe sleeve 106 during a reprocessing step, the fluid flowing through the circulation conduit 21 is not restricted, and thus it is not possible to detect the detachment of the endoscope-side connector portion 34 based on the flow rate measured by the flow sensor 23.

In contrast, according to the present embodiment, if the endoscope-side connector portion 34 comes off the pipe sleeve 106, the pressure-receiving portion 43 provided in the endoscope-side connector portion 34 blocks up the fluid introduction port 35a, making it possible to detect the detachment of the endoscope-side connector portion 34 based on the flow rate measured by the flow sensor 23. Note that components having the same functions as those in the first embodiment are denoted by the same reference numerals as the corresponding components in the first embodiment, and detailed description thereof will be omitted.

A linkage mechanism 41B according to the present embodiment includes a pressure-receiving portion 43, a first link portion 51, a second link portion 52a, and a third link portion 52b, and one end of the first link portion 51 is supported on an inner circumference of the opening portion 37c opening to the movable portion 37. Also, the other end of the first link portion 51 is connected to a pivot point of the second link portion 52a and third link portion 52b. The second and third link portions 52a and 52b are lever links functioning as lock portions. The second link portion 52a is extended from a site of support and connection with the third link portion 52b in a direction opposite the fluid introduction port 35a and is supported by the inner wall of the housing portion 35. On the other hand, the third link portion 52b is extended from a site of support and connection with the second link portion 52a in a direction of the fluid introduction port 35a and is supported by lower back part of the pressure-receiving portion 43. Also, an elastic member 43c is bonded to an end edge of an opening of the pressure-receiving portion 43.

Incidentally, on the inner wall of the housing portion 35, a horizontal section below the spring catching portion 35c is formed into a circular shape, a horizontal section above the spring catching portion 35c is formed into a rectangular shape, and the fluid introduction port 35a opens to a rectangular flat surface.

Also, as shown in FIG. 10, in a state (first state) in which the second and third link portions 52a and 52b are placed in line with each other, the pressure-receiving portion 43 is pressed from behind in the direction of the fluid introduction port 35a and the elastic member 43c bonded to the end edge of the opening of the pressure-receiving portion 43 is pressed against an inner wall of an outer circumference of the fluid introduction port 35a restraining the pivoting of the pressure-receiving portion 43 and blocking the fluid introduction port 35a in this state. Also, the elastic member 43c is designed to deform elastically to absorb any backlash produced in respective connecting parts of the second and third link portions 52a and 52b placed in line with each other. Consequently, the pressure-receiving portion 43 remains pressed against the outer circumference of the fluid introduction port 35a without displacement.

Also, in the first state, the sealing portion 37b of the movable portion 37 is located at the third position p3 where the sealing portion 37b abuts the top face of the locking portion 36a formed on the hook portion 36, and consequently movement of the first link portion 51 in the direction of the fluid lead-out port 35b is restricted and the linear state of the second and third link portions 52a and 52b connected to the first link portion 51 remains locked.

With this configuration, as shown in FIG. 10, when the endoscope-side connector portion 34 is not fitted to the pipe sleeve 106 or when the endoscope-side connector portion 34 comes off after being fitted to the pipe sleeve 106, as the movable portion 37 moves in the direction of the fluid lead-out port 35b under the urging force of the compression spring 44, the first link portion 51 supported on the inner circumference of the opening portion 37c of the movable portion 37 via a support pin moves in the same direction and causes the second and third link portions 52a and 52b to pivot downward.

Then, when the sealing portion 37b of the movable portion 37 abuts the top face of the locking portion 36a formed on the hook portion 36 (third position p3), the second and third link portions 52a and 52b are locked in the linear arrangement. Then, the back of the pressure-receiving portion 43 is pressed in the direction of the fluid introduction port 35a by the second and third link portions 52a and 52b and the elastic member 43c bonded to the open end portion of the pressure-receiving portion 43 is pressed against the fluid introduction port 35a (first state).

When the fluid is supplied from the side of the tube main body 32 of the cleaning tube 31, the fluid applies fluid pressure to the pressure-receiving surface 43b of the pressure-receiving portion 43 blocking up the fluid introduction port 35a, but since the back of the pressure-receiving portion 43 is locked in a state of being pressed by the second and third link portions 52a and 52b extending out rectilinearly, the fluid introduction port 35a remains blocked, restricting the flow rate of the fluid.

Thus, the flow rate measured by the flow sensor 23 interposed in the circulation conduit 21 (see FIG. 2) decreases extremely, making it possible to check connected conditions (detachment after connection) of the endoscope-side connector portion 34 with the pipe sleeve 106 based on the flow rate.

Also, when the flange portion 106b of the pipe sleeve 106 is fitted over the hook portion 36 provided in lower part of the endoscope-side connector portion 34, the bottom face of the movable portion 37 moves by being pressed upward by the open end of the pipe sleeve 106, causing the movable portion 37 to move to the second position p2. Consequently, the first link portion 51 connected to the movable portion 37 via a support pin is pressed in the same direction, pressing a supporting portion where the second and third link portions 52a and 52b are connected with each other.

As a result, a connecting site between the second and third link portions 52a and 52b moves upward, releasing the lock, and consequently the third link portion 52b pulls the pressure-receiving portion 43 backward. Consequently, with the upper bracket 43a being supported by the suspension bracket 35d, the pressure-receiving portion 43 pivots in a counterclockwise direction in FIG. 11, opening the fluid introduction port 35a (second state).

Then, when the fluid is introduced into the housing portion 35 from a side of the cleaning tube 31, the fluid pressure is applied to the pressure-receiving surface 43b of the pressure-receiving portion 43, causing the pressure-receiving portion 43 to further pivot in the counterclockwise direction and thereby enter a third state. Then, the pressure-receiving portion 43 pushes up the third link portion 52b, and the movable portion 37 is pulled upward against the urging force of the compression spring 44 via the first link portion 51 connected to the third link portion 52b. As a result, as shown in FIG. 11, the gap s1 larger than the height h1 (see FIG. 7) of the flange portion 106b of the pipe sleeve 106 is formed between the locking portion 36a of the hook portion 36 and a bottom portion of the movable portion 37, and the circumference of the pipe sleeve 106 is cleaned or disinfected by the fluid flowing through the gap s1. At this time, the bottom face of the movable portion 37 is located at the first position closer to the side of the fluid introduction port 35a than the second position described above.

On the other hand, if the conduit in the endoscope 101 clogs, since the fluid stagnates in the housing portion 35, increasing the internal pressure of the housing portion 35, the movable portion 37 is pushed down by the internal pressure and the urging force of the compression spring 44, causing the sealing portion 37b provided on the bottom face to abut the open end of the pipe sleeve 106 (second position p2), and thereby limiting leakage of the fluid from around the pipe sleeve 106.

As a result, since the flow rate of the fluid flowing through the circulation conduit 21 is decreased extremely, clogging of the conduit in the endoscope 101 can be detected with high accuracy based on the flow rate measured by the flow sensor 23 interposed in the circulation conduit 21.

Note that at this time, at the second position p2 where the sealing portion 37b provided on the bottom face of the movable portion 37 abuts the open end of the pipe sleeve 106, the first link portion 51 causes the pressure-receiving portion 43 to pivot to the side of the fluid introduction port 35a via the second and third link portions 52a and 52b. As a result, as shown in FIG. 12, the pressure-receiving portion 43 enters a second state in which opening area between the elastic member 43c bonded to the open end of the pressure-receiving portion 43 and the fluid introduction port 35a is narrowed down, limiting inflow of the fluid into the housing portion 35.

In this way, being capable of detecting not only clogging of a conduit in the endoscope 101, but also detachment of the endoscope-side connector portion 34 from the pipe sleeve 106, the present embodiment makes it possible to check easily whether the endoscope-side connector portion 34 properly is fitted in the pipe sleeve 106, and thereby provide high reliability.

Third Embodiment

A third embodiment of the present invention is shown in FIG. 13 to FIG. 20. According to the present embodiment, a cam link mechanism 41C is disposed in the endoscope-side connector portion 34, being configured to form or block a gap between the cam link mechanism 41C and pipe sleeve 106. Note that components having the same functions as those in the first embodiment are denoted by the same reference numerals as the corresponding components in the first embodiment, and detailed description thereof will be omitted.

Figure 15:
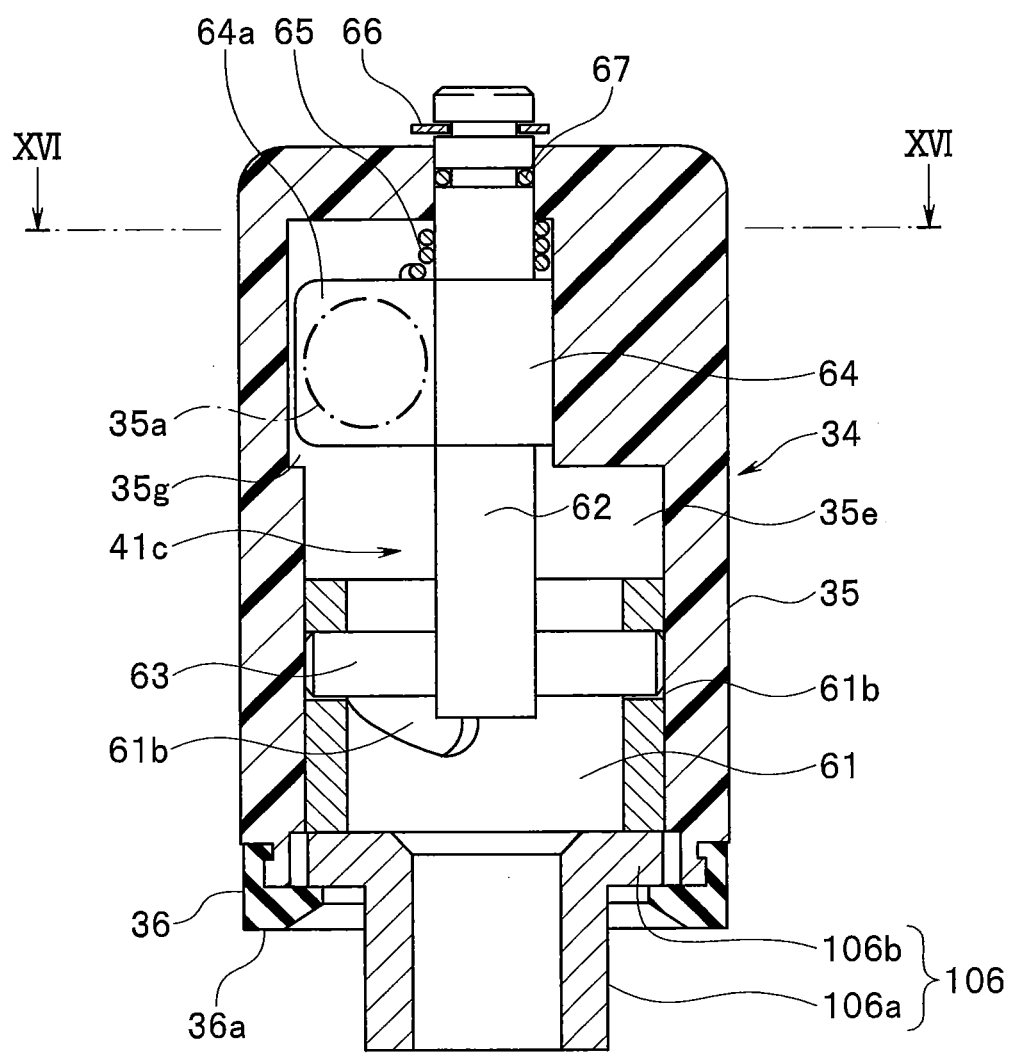
FIG. 15 a sectional front view of the endoscope-side junction of the cleaning tube according to the third embodiment.

That is, as shown in FIG. 15, the cam link mechanism 41C provided in the housing portion 35 has a cylindrical movable portion 61 in lower part, convex guide portions 61a are formed at symmetrical positions on an outer circumference of the cylindrical movable portion 61, extending in the up-and-down direction, and cam slots 61b are formed at opposite positions on the outer circumference. Furthermore, a cam pin 63 provided at a lower end of a rotating shaft 62 is passed through the cam slots 61b, extending out in a direction orthogonal to the shaft. Also, a pressure-receiving portion 64 is fixedly installed in upper part of the rotating shaft 62, and a pressure-receiving surface 64a is formed in a tabular shape on one side of the pressure-receiving portion 64.

On the other hand, in lower part in the housing portion 35, a space 35e is formed to permit movement of the cylindrical movable portion 61 in the up-and-down direction and guide grooves 35f are formed in an inner wall of the housing portion 35 to support the convex guide portions 61a slidably in the up-and-down direction, where the convex guide portions 61a are formed on the outer circumference of the cylindrical movable portion 61. Also, in upper part in the housing portion 35, a guiding space 35g is formed to permit pivoting of the pressure-receiving surface 64a configured to pivot in a rotational direction and, moreover, a locking end portion 35h is formed in the guiding space 35g as shown in FIG. 16 to restrict an initial position of the pressure-receiving surface 64a by latching onto the pressure-receiving surface 64a.

A torsion spring 65, which is an example of a spring portion, is axially mounted above the pressure-receiving portion 64 on the rotating shaft 62, latched at one end onto the pressure-receiving surface 64a, and latched at the other end onto the inner wall of the housing portion 35. Note that spring pressure of the torsion spring 65 is set at a value smaller than the pressure of the fluid introduced into the housing portion 35.

Figure 18:
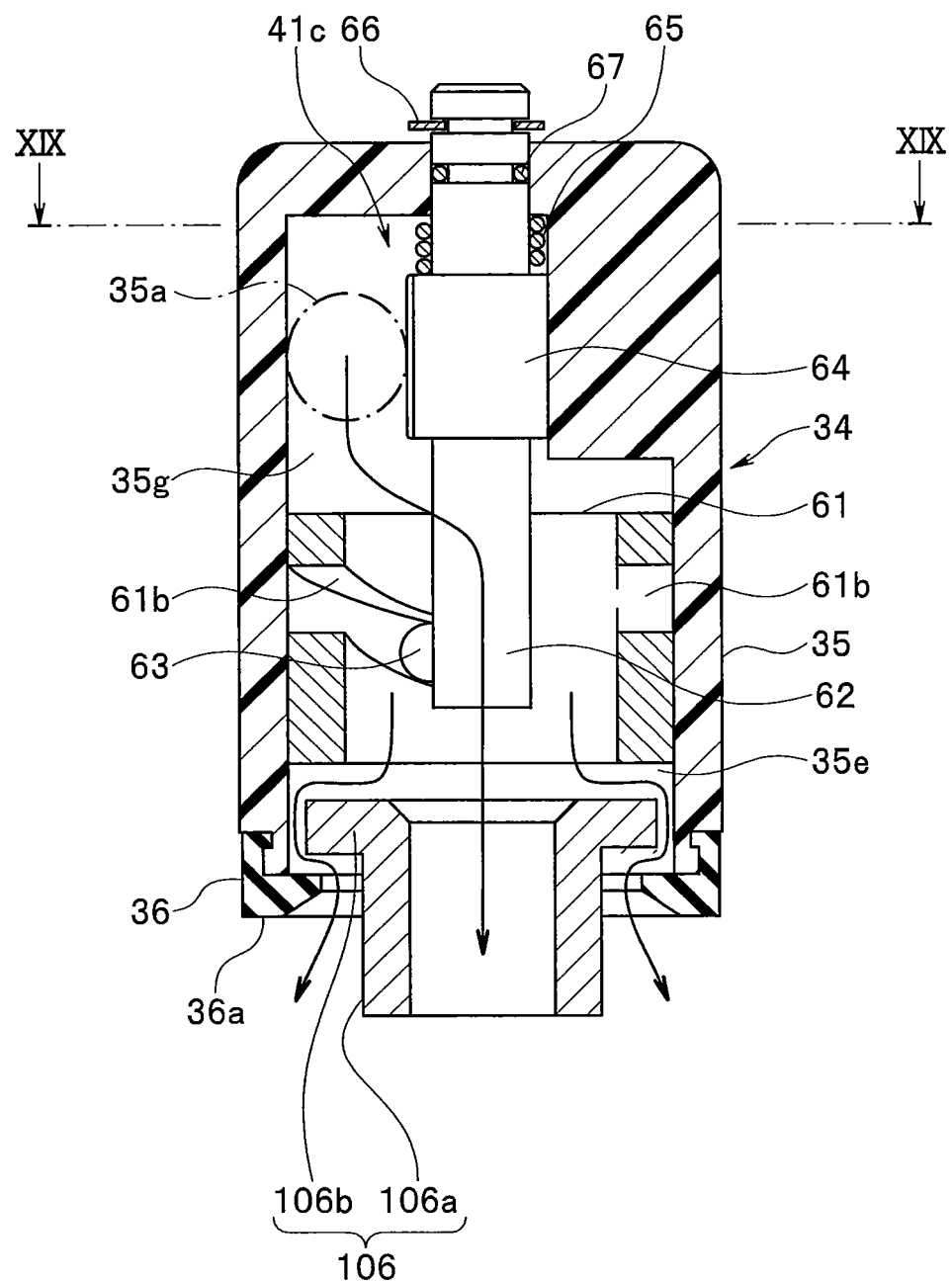
FIG. 18 is a sectional front view of how the endoscope-side junction of the cleaning tube is connected to the pipe sleeve of the endoscope according to the third embodiment.

Furthermore, upper part of the rotating shaft 62 is passed through the housing portion 35 and pivotably supported, an upper end protrudes from the housing portion 35, and an E-shaped ring 66 is fitted over the protrusion as a retainer. Also, as shown in FIG. 15 and FIG. 18, a portion pivotably supporting the rotating shaft 62 of the housing portion 35 is sealed by a seal ring 67.

Figure 16:
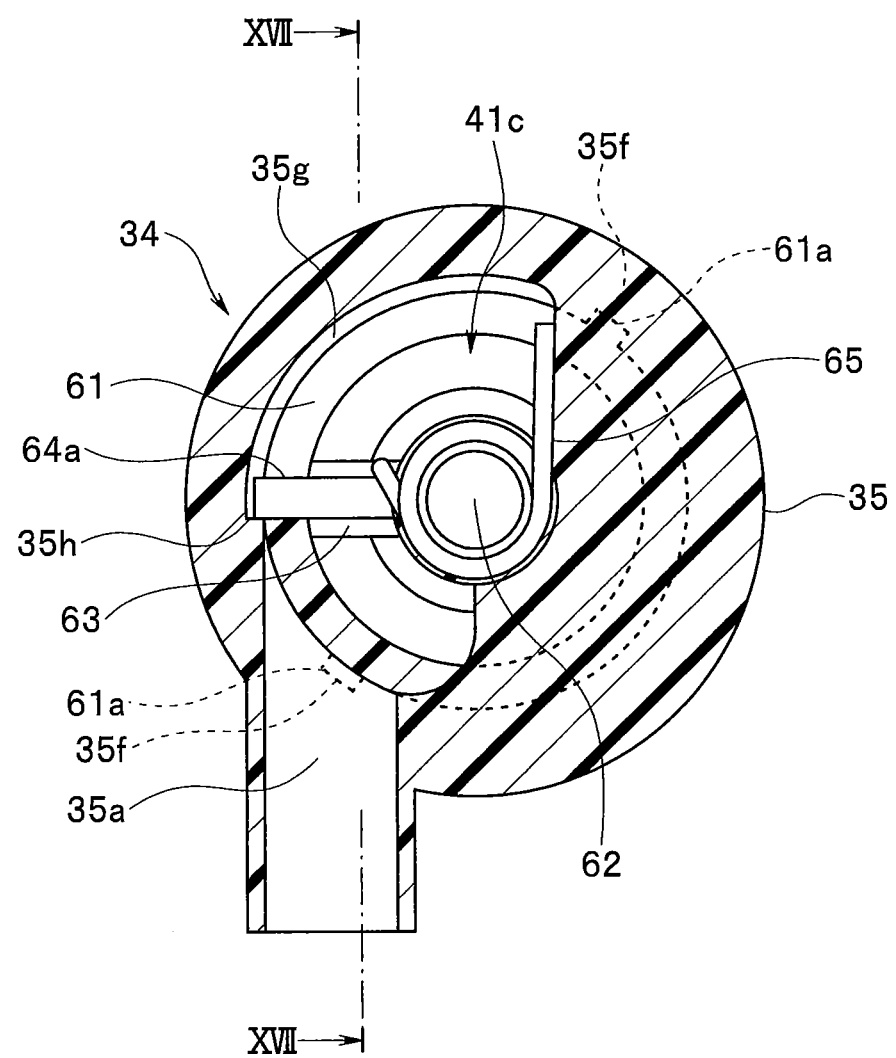
FIG. 16 is a sectional view taken along line XVI-XVI in FIG. 15, according to the third embodiment.

As shown in FIG. 16, the torsion spring 65 constantly urges the rotating shaft 62 in a counterclockwise direction in FIG. 16, causing a tip portion of the pressure-receiving surface 64a to be latched by the locking end portion 35h formed in a counterclockwise direction of the guiding space 35g, and thereby restricting the initial position of the pressure-receiving surface 64a. On the other hand, as shown in FIG. 15 and FIG. 16, the fluid introduction port 35a is oriented in a direction opposite and approximately orthogonal to the pressure-receiving surface 64a to cause the fluid to collide directly with the pressure-receiving surface 64a in a state of initial position.

Figure 17:
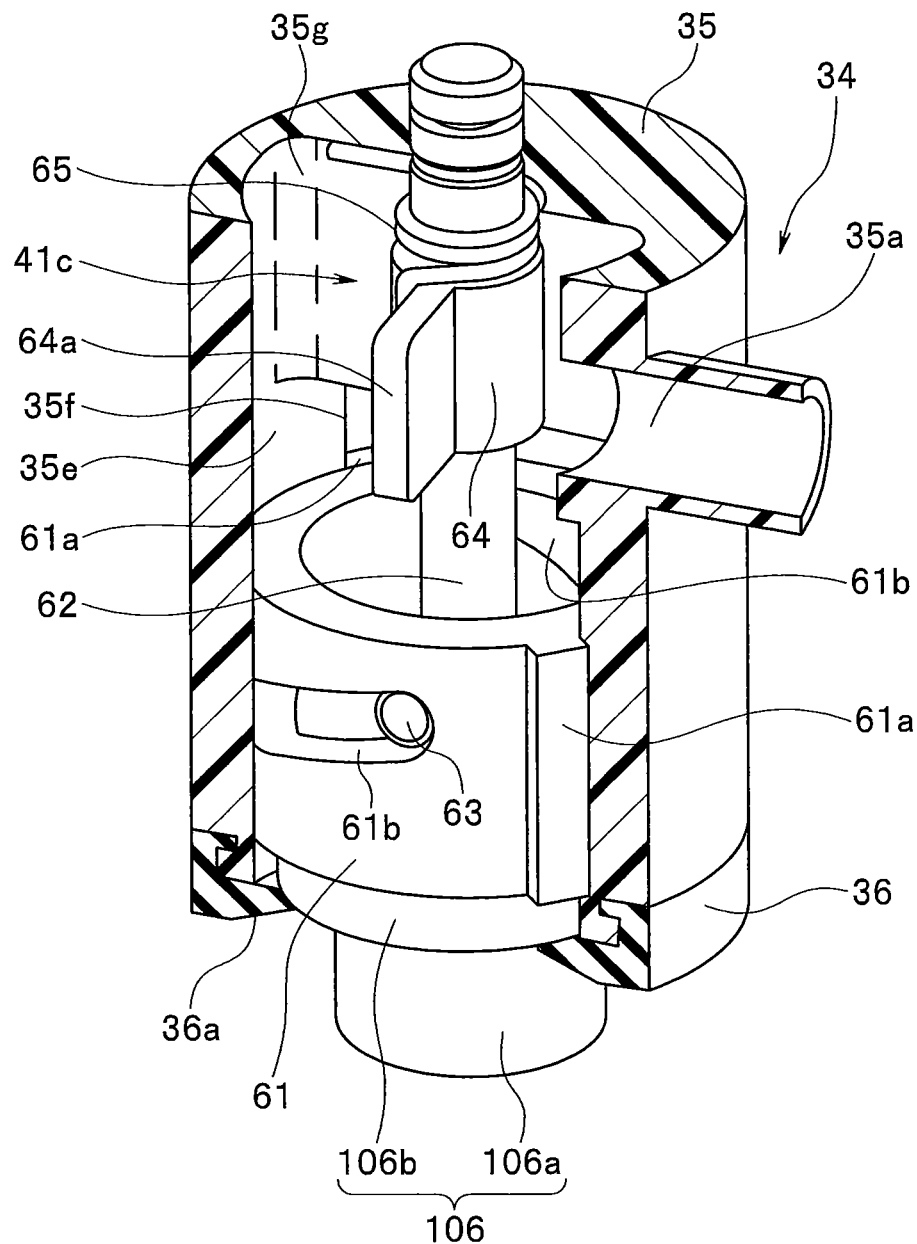
FIG. 17 is a sectional perspective view taken along line XVII-XVII of FIG. 16, according to the third embodiment.

Also, as shown in FIG. 15 and FIG. 17, when the pressure-receiving surface 64a is in a state of initial position, a bottom face of the cylindrical movable portion 61 is set at such a position as to abut an open end of the flange portion 106b of the pipe sleeve 106 fitted over the hook portion 36, and at this time, the cam pin 63 is passed through upper part of the cam slots 61b formed in the cylindrical movable portion 61. Thus, according to the present embodiment, the cam slots 61b formed in the cylindrical movable portion 61 are shaped so as to move the cylindrical movable portion 61 upward when the rotating shaft 62 rotates in a clockwise direction in FIG. 16.

Figure 13:
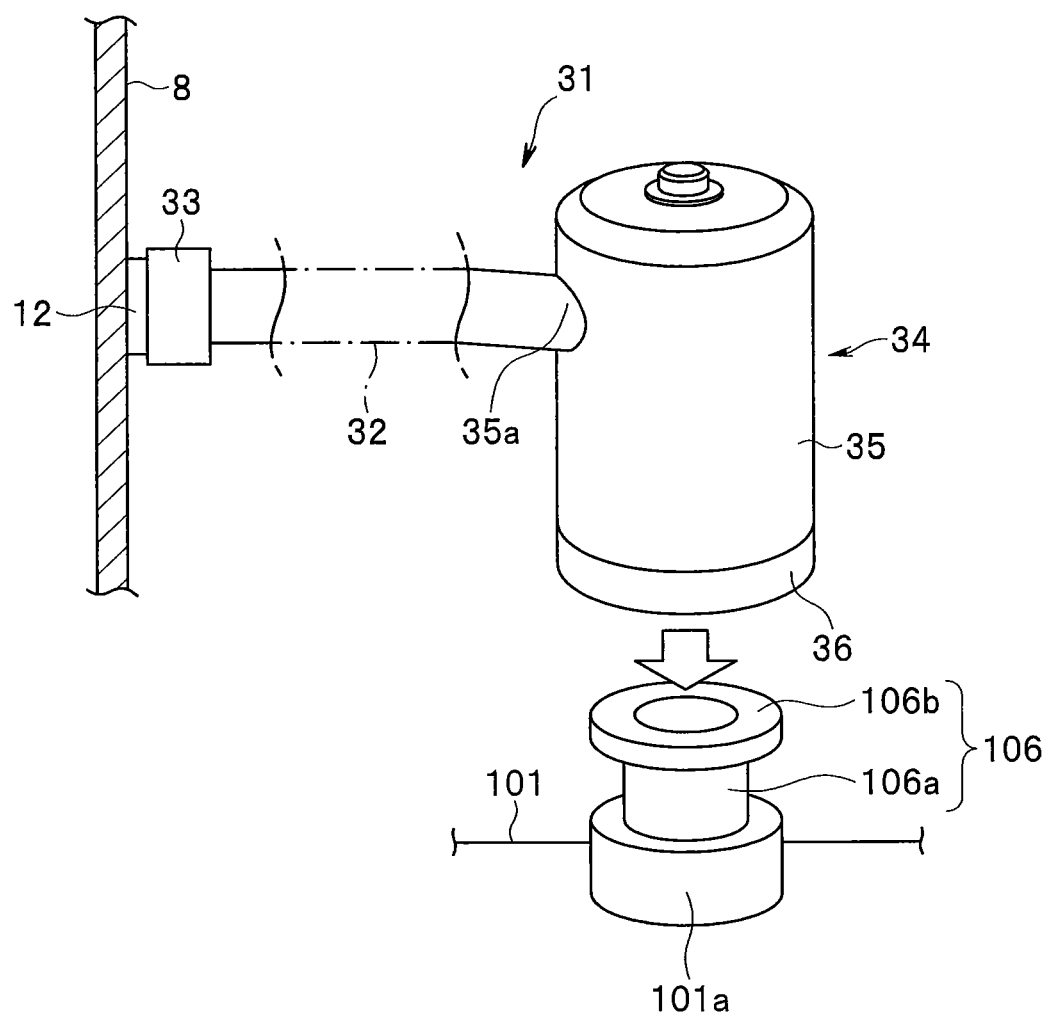
FIG. 13 is a perspective view of how an endoscope-side junction of a cleaning tube is connected to a pipe sleeve of an endoscope according to a third embodiment.
Figure 14:
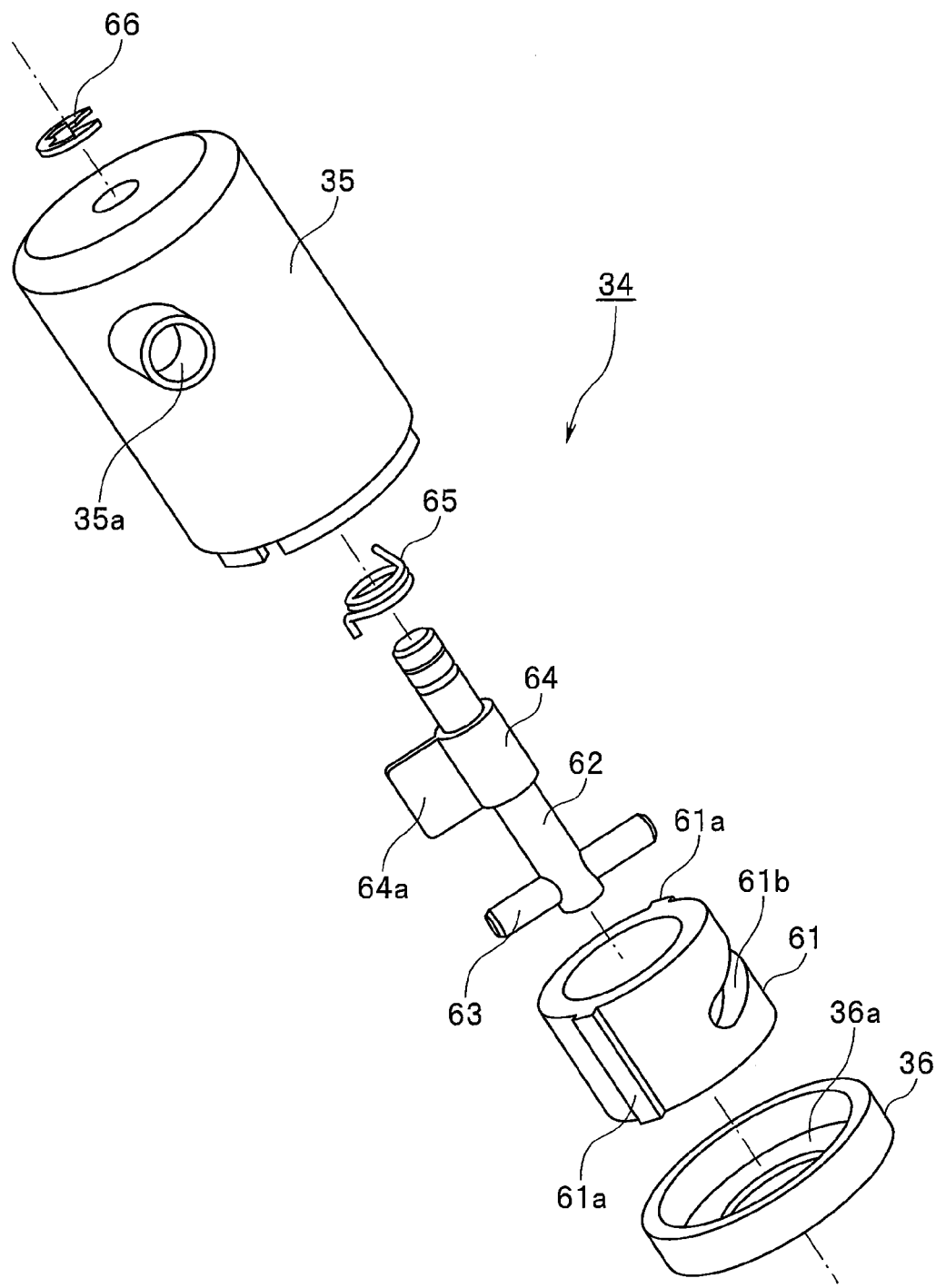
FIG. 14 is an exploded perspective view of the endoscope-side junction of the cleaning tube according to a third embodiment.

With this configuration, when the hook portion 36, such as shown in FIG. 13, provided in lower part of the endoscope-side connector portion 34 is fitted in the flange portion 106b of the pipe sleeve 106 provided in the opening portion 101a communicated with each conduit in the endoscope 101, a lower end of the cylindrical movable portion 61 abuts the open end of the flange portion 106b as shown in FIG. 15.

Then, in this state, when the fluid is supplied into the housing portion 35 through the tube main body 32 of the cleaning tube 31, since the fluid introduction port 35a in the housing portion 35 is oriented in the direction opposite and approximately orthogonal to the pressure-receiving surface 64a of the pressure-receiving portion 64 located at the initial position, the fluid pressure of the fluid is applied to the pressure-receiving surface 64a. Consequently, the pressure-receiving surface 64a is pressed in the clockwise direction in FIG. 16 against an urging force of the torsion spring 65, causing the rotating shaft 62 having the pressure-receiving portion 64 at one end to pivot in the same direction. Consequently, the cam pin 63 provided so as to protrude from the lower part of the rotating shaft 62 moves in the same direction in the cam slots 61b formed in the cylindrical movable portion 61, causing the cylindrical movable portion 61 to move upward via the cam slots 61b. Note that the cylindrical movable portion 61 does not move rotationally because the convex guide portions 61a formed on the outer circumference of the cylindrical movable portion 61 are inserted in the guide grooves 35f formed in the inner wall of the housing portion 35 in such a way as to be permitted to move in the up-and-down direction.

Figure 19:
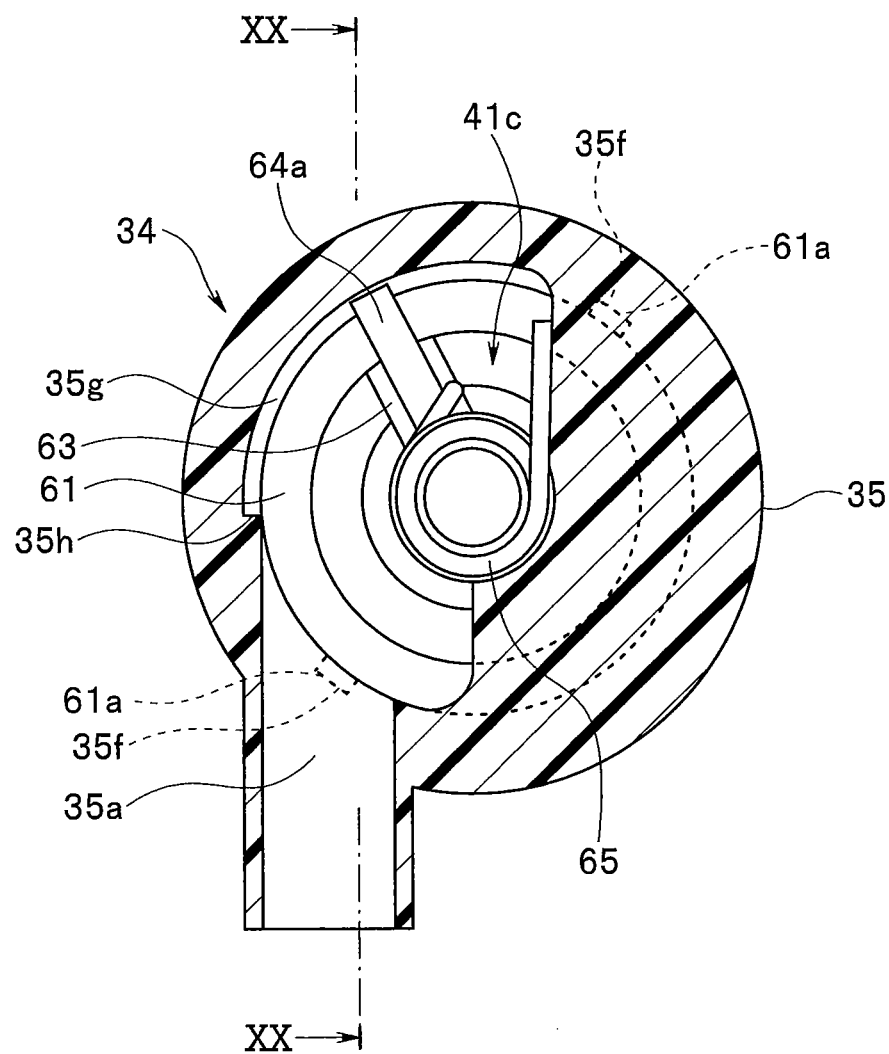
FIG. 19 is a sectional view taken along line XIX-XIX of FIG. 18, according to the third embodiment.
Figure 20:
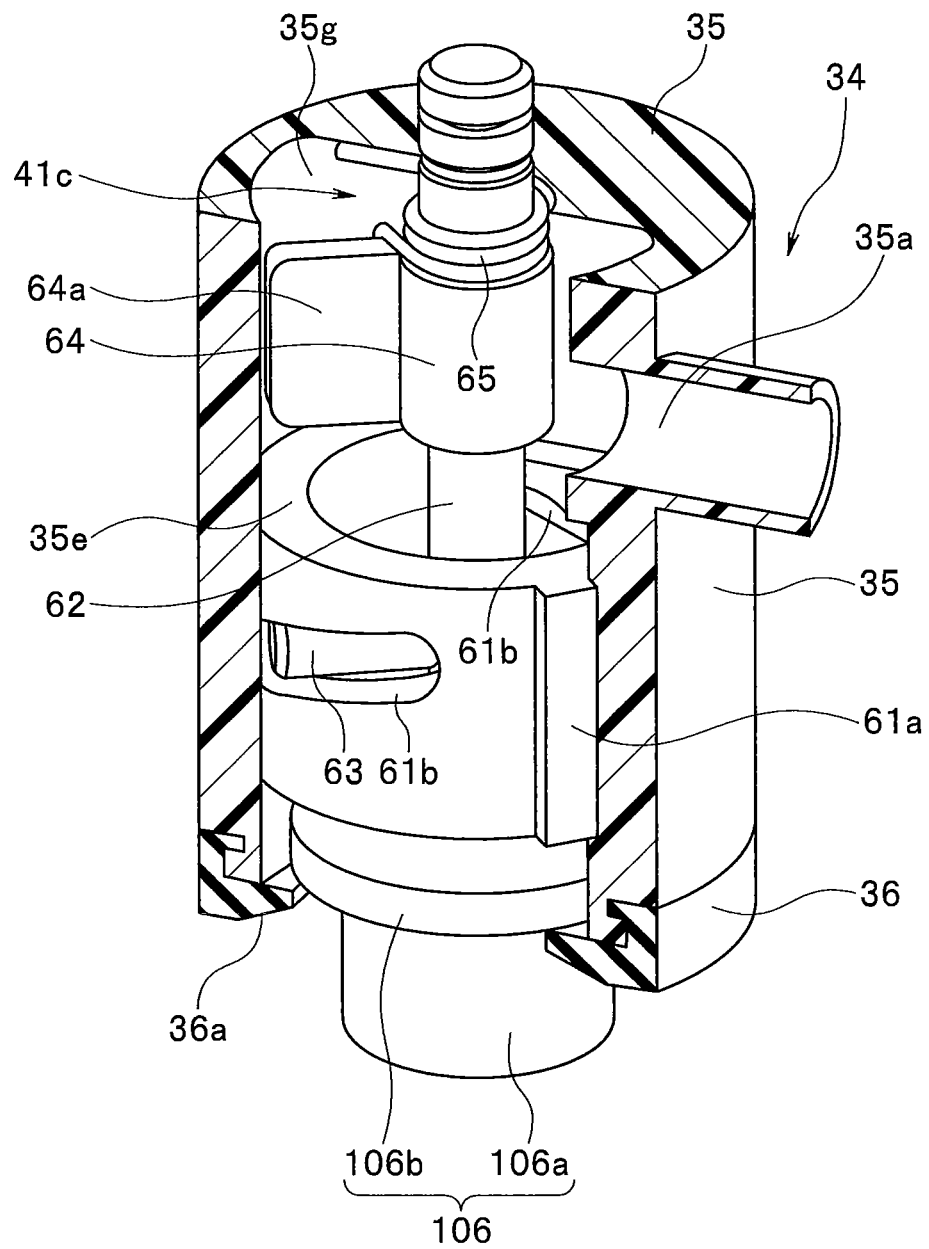
FIG. 20 is a sectional view taken along line XX-XX of FIG. 19, according to the third embodiment.

Consequently, as shown in FIGS. 18 to 20, the bottom face of the cylindrical movable portion 61 gets spaced away from the open end of the flange portion 106b of the pipe sleeve 106, forming a space between the locking portion 36a formed on the hook portion 36 and the cylindrical movable portion 61 to pass fluid, and the circumference of the pipe sleeve 106 is cleaned or disinfected by the fluid flowing through the space. Also, the interior of the conduit is cleaned or disinfected by the fluid flowing from the pipe sleeve 106 into the conduit.

On the other hand, if the conduit is clogged, since the fluid stagnates in the housing portion 35, the fluid pressure applied to the pressure-receiving surface 64a falls gradually. Then, when the spring pressure of the torsion spring 65 exceeds the fluid pressure applied to the pressure-receiving surface 64a and the loads caused by frictional resistance of respective sliding parts, the torsion spring 65 causes the rotating shaft 62 to pivot in a counterclockwise direction in FIG. 19, returning the pressure-receiving surface 64a to the initial position shown in FIG. 16.

Consequently, the cam pin 63 passed through the cam slots 61b of the cylindrical movable portion 61 causes the cylindrical movable portion 61 via the cam slots 61b to slide downward and causes the lower end of the cylindrical movable portion 61 to abut the open end of the pipe sleeve 106 as shown in FIG. 15. As a result, since leakage of the fluid from around the pipe sleeve 106 is limited, extremely decreasing the flow rate measured by the flow sensor 23 (see FIG. 2) interposed in the circulation conduit 21, clogging of the conduit in the endoscope 101 can be detected with high accuracy based on the flow rate.

In this way, according to the present embodiment, since the cylindrical movable portion 61 is caused to move up and down via the cam link mechanism 41C connected to the rotating shaft 62 adapted to pivot under fluid pressure, when the cylindrical movable portion 61 is abutted against upper part of the pipe sleeve 106 due to clogging in the conduit of the endoscope 101, the cylindrical movable portion 61 does not move upward greatly under influence of external vibration and the open end of the pipe sleeve 106 can be kept blocked by the bottom face of the cylindrical movable portion 61. Note that an elastic member may be bonded to the bottom face of the cylindrical movable portion 61 to increase adhesion to an open end portion of the pipe sleeve 106.

What is claimed is:

1. An endoscope cleaning tube comprising:
    a housing portion equipped with a fluid introduction port adapted to introduce a fluid and a fluid lead-out port adapted to lead out the fluid introduced through the fluid introduction port;
    a hook portion extending out from an outer surface of the housing portion in a lead-out direction of the fluid to connect the housing portion to a pipe sleeve;
    a movable portion placed movably between a first position and a second position in the housing portion, being equipped with a partition portion adapted to divide an inner part of the housing portion into a side of the fluid introduction port and a side of the fluid lead-out port and with an opening portion which is an opening provided in the partition portion, the second position being located closer to the side of the fluid lead-out port than the first position;
    a pressure-receiving portion which, being equipped with a pressure-receiving surface placed at a position facing the fluid introduction port and adapted to receive pressure of the introduced fluid and with a first end portion pivotably connected to an inner wall of the housing portion, is adapted to pivot according to an amount of the fluid pressure acting on the pressure-receiving surface; and
    a linking portion adapted to connect the pressure-receiving portion and the movable portion with each other and move the movable portion from the second position to the first position along with pivoting of the pressure-receiving portion when the pressure-receiving portion receives fluid pressure equal to or larger than a predetermined amount.

2. The endoscope cleaning tube according to claim 1, further comprising a spring portion placed in the housing portion and adapted to urge the movable portion toward the fluid lead-out port.

3. The endoscope cleaning tube according to claim 1, wherein:
    the pressure-receiving surface is positioned to close the fluid introduction port;
    the linking portion comprises a lock portion adapted to connect the housing portion and pressure-receiving portion with each other, configured to be transformable to a first state and a second state, and adapted to restrain pivoting of the pressure-receiving portion by pressing the pressure-receiving surface against the fluid introduction port when placed in the first state, and release the pressing when placed in the second state; and
    a first linking portion adapted to connect the lock portion and the movable portion, the first linking portion bringing the lock portion to the first state when the movable portion is located at a third position closer to a fluid lead-out port than the second position, and bringing the lock portion from the first state to the second state when the movable portion moves from the third position to the second position.

* * * * *